(12) United States Patent
Lazar

(10) Patent No.: US 7,744,762 B2
(45) Date of Patent: Jun. 29, 2010

(54) MICROFLUIDIC DEVICES AND METHODS FACILITATING HIGH-THROUGHPUT, ON-CHIP DETECTION AND SEPARATION TECHNIQUES

(75) Inventor: Iuliana M. Lazar, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 618 days.

(21) Appl. No.: 11/466,818

(22) Filed: Aug. 24, 2006

(65) Prior Publication Data
US 2008/0073506 A1    Mar. 27, 2008

(51) Int. Cl.
*B01D 15/08* (2006.01)
*C02F 1/28* (2006.01)
*G01N 30/02* (2006.01)

(52) U.S. Cl. .................. 210/656; 210/198.2; 210/659; 422/70

(58) Field of Classification Search ............. 210/198.2, 210/656
See application file for complete search history.

(56) References Cited

U.S. PATENT DOCUMENTS

| | | | |
|---|---|---|---|
| 5,705,813 A * | 1/1998 | Apffel et al. ............. | 250/288 |
| 6,849,396 B2 * | 2/2005 | Schneider .................. | 435/4 |
| 6,915,679 B2 * | 7/2005 | Chien et al. ............... | 73/54.01 |
| 2002/0170825 A1 | 11/2002 | Lee et al. | |
| 2002/0186263 A1 * | 12/2002 | O'Connor et al. .......... | 346/7 |
| 2002/0187074 A1 * | 12/2002 | O'Connor et al. .......... | 422/82.05 |
| 2002/0195342 A1 | 12/2002 | Lee et al. | |
| 2004/0208751 A1 * | 10/2004 | Lazar et al. ............... | 417/48 |

FOREIGN PATENT DOCUMENTS

WO    WO03092846    11/2003

* cited by examiner

Primary Examiner—Krishnan S Menon
Assistant Examiner—Katherine Zalasky
(74) Attorney, Agent, or Firm—Whitham Curtis Christofferson & Cook, PC

(57) ABSTRACT

The present invention provides a microfluidic device and method for facilitating on-chip complex sample processing and detection. In general, the device comprises at least a separation channel of a separation system, an interface, and an array of microreservoirs disposed within the same chip. The interface is configured to orthogonally transfer separated components from the separation channel into the array of microreservoirs, enabling direct analyte detection from the chip and high-throughput analysis.

34 Claims, 11 Drawing Sheets

MICROFLUIDIC DEVICES AND METHODS FACILITATING HIGH-THROUGHPUT, ON-CHIP DETECTION AND SEPARATION TECHNIQUES

This invention was made with government support under Grant # BES0448840 awarded by the National Science Foundation. The government has certain rights in the invention.

BACKGROUND OF THE INVENTION

1. Field of the Invention

The present invention generally relates to microfluidic devices and methods for use, and more particularly, to high-throughput microfluidic devices and methods for on-chip complex biological and/or chemical sample separation and/or detection of separated components.

2. Discussion of Related Art

Cancer is a leading cause of death in the U.S. and throughout the world, with over 1,000,000 new cases being diagnosed every year in the U.S. alone. Hundreds of genes are involved in the development of diseases such as cancer. An accumulation of mutations, which result in loss- or over-expression of genes that control cell growth and proliferation, ultimately lead to the onset of the disease. To fully elucidate the molecular mechanisms and pathways that govern cancer initiation and progression, the information generated at the DNA and mRNA level must be complemented with a complete and detailed panorama of protein expression levels and their post-translational modifications. The characterization of the proteomic complement of a specific genome will enable us to understand the basic processes that distinguish healthy versus diseased states.

The analysis of proteomic samples is very difficult, however, for a number of reasons. First, the sample is either available in a limited amount (e.g., a few thousands of cells to start with), or the final subfractions submitted to analysis are extremely small (e.g., 1-10 µl at the nM/pM concentration level). Second, the sample itself is typically complex (5,000-10,000 different proteins may be expressed in a mammalian cell at any given time). Third, the dynamic range of the proteins present is typically very large ($1:10^6$) and/or their presence easily obscured by other more highly abundant components.

In order to contend with the overwhelming numbers of mixture components, complex samples are typically separated (i.e., fractionated) into smaller components prior to analysis. Two common types of separation techniques include: "gel-based" (e.g., 2D Polyacrylamide Gel Electrophoresis "2D-PAGE"); and "liquid chromatography (LC)-based" (e.g., 2D Strong Cation Exchange "SCX" and High Performance Liquid Chromatography "HPLC") approaches. Comparatively, 2D-PAGE is a relatively awkward and time consuming separation technique that utilizes a gel to separate proteins according to isoelectric point, or charge, in a first dimension, and according to molecular weight, or size, in a second dimension. LC techniques utilize a stationary phase and a mobile phase to separate sample components based on properties, such as hydrophobicity, charge, and size. LC operates such that the sample to be separated is initially loaded at the head of a separation channel packed with a stationary phase, and then forced through the channel with the aid of a mobile phase under high pressure. The sample components are separated according to their differential interaction with the packing material (the stationary phase) in the channel. In 2D-LC, for example, the sample is separated according to charge in the first dimension and according to hydrophobicity in the second dimension. Several notable advantages of 2D-LC over the more complicated 2D-PAGE process include: easier automation, no gel handling, better separation power, and simpler coupling to other techniques, such as mass spectrometry.

Mass Spectrometry (MS) is a detection technique commonly used following the above mentioned separation techniques. MS is used to detect sample components with a higher degree of detail by generating a mass spectrum representing masses of individual components. In addition, MS is highly suited for proteomic investigations for a number of reasons: 1) it generates results with a level of confidence that is comparable to amino acid sequencing of electrophoretically separated proteins; 2) it is more tolerant towards low molecular contaminants; and 3) it is faster, simpler, and more sensitive than traditional sequencing protocols. As a result, MS has evolved into the detection tool of choice for proteomic applications (refs [1-5]) as it offers the combined benefits of specificity, sensitivity, resolving power, and capability to deliver high quality structural information. In many cases, routine MS analysis can be performed from protein quantities as low as 10-100 fmol; and state-of-the-art MS is demonstrating results at the amol level.

Other recent improvements in MS detection sensitivity and analysis speed have launched this technique into an effective strategy for the detection of novel disease biomarkers and protein co-expression patterns. Current approaches for biomarker discovery and/or screening involve techniques such as DNA microarray technology, immunohistochemical staining, protein chips, and multidimensional separations followed by MS detection. These approaches, however, are accompanied by numerous limitations that include: insufficient quantitative correlation between gene and protein expression level; complexity and lengthiness for analytical approaches that attempt comprehensive qualitative/quantitative proteomic profiling; and lack of sufficient sensitivity, specificity and reproducibility.

Mass spectrometry generally operates by initially ionizing the sample within an ionization source, separating the ions of differing masses, and recording their relative abundance with a mass spectrometer. In particular, two commonly used MS ionization techniques include: Electrospray ionization (ESI) and Matrix Assisted Laser Desorption Ionization (MALDI). ESI operates by generating gas-phase ions (or "spray") from a liquid phase solution. According to this technique, an analyte solution is pumped through a very small charged capillary such that the liquid exits the capillary in the form of an aerosol or mist. After a series of subsequent charge-based interactions, the aerosol droplets eventually reach the mass spectrometer in the form of lone ions for detection. MALDI, on the other hand, is an ionization technique that mixes a matrix solution with the sample (or analyte) to produce a homogeneous co-crystallized analyte-matrix solution. Specifically, the role of the matrix is to absorb the energy of a laser beam and transfer it to the more fragile analyte molecules. Advantages of MALDI-MS include: amenability to high-throughput, ease of operation, and applicability for fast peptide mapping. Recently, MS/MS sequencing techniques that enable unambiguous peptide identifications have been developed for MALDI-MS as well. However, some challenges toward this end include developing simple, compact, and low cost devices with parallel processing capabilities that would enable high-throughput investigations.

Interestingly, miniaturization is emerging as a significant trend in analytical and biological instrumentation (refs [6-8]). One unique benefit of miniaturization is that a variety of novel analytical configurations only become possible if they are developed in a microfabricated format. For example, high-speed capillary electrophoresis (CE) can be performed on a microchip device in as fast as 0.8 ms using a separation channel of only 200 µm in length (ref 9). Moreover, microchips can handle as little as 1-5 microliters (µl) of sample, analyze volumes as low as 1 pl-1 nl, and perform sample injection, labeling, and detection within millisecond timeframes (ref 9). Additionally, the micro-domain environment enables the emergence of unique physical events. Particularly, as the size of a device decreases, the surface-to-volume ratio increases. As a result, surface driven phenomena begin to dominate in the micro-scale world. Electroosmotic flow (EOF), which can be effectively generated only in capillaries with dimensions in the micrometer (um) domain, represents a relevant example.

Microfluidic devices function according to well-established principles and are characterized by several features that distinguish them from large-scale instrumentation. First, the miniature format of these devices enables the manipulation of extremely small sample amounts and short analysis times, resulting in significantly reduced analysis costs. Second, the ability to perform precise and accurate sample handling operations with microfluidic devices advantageously enables process control and automation, and the generation of reliable and high-quality data. Finally, microfabrication enables large-scale integration, multiplexing, and consequently high-throughput analysis. In addition, microfluidic devices may be fabricated from several different materials that include glass, quartz, polymeric and silicon substrates (refs 6,8), and may comprise a variety of elements that perform operations, such as pumping, dispensing, clean up, mixing, separation, chemical alterations, and detection (ref 7).

Despite the advantages of microfluidic devices, very few have been successfully combined with MS analysis (refs 10-30). In addition, because MS/MS capabilities were only available until recently with ESI-MS, the microchips that have been developed have been primarily interfaced with ESI. Such microchip-ESI interfaces typically allow ESI to be generated either: directly from the chip surface (refs 10-12); from capillary emitters inserted in the chip (13-18); or from microfabricated emitters (refs 19-22). Liquid sheath, liquid junction and nano-ESI sources have been implemented (refs 17-23). However, the bottleneck of all these applications goes back to the sequential nature of traditional ESI-MS detection. Conversely, microfluidic technologies that enable high-throughput MALDI-MS detection remain in a very early stage of development. These technologies typically make use of a piezo-actuated flow-through dispenser (refs 24,25) or a centrifugal CD (refs 31,32). For example, microfabricated piezo-actuated flow-through dispensers can be used to deposit samples on a nanovial target plate and to interface capillary liquid chromatography to MALDI/TOF (refs 24,25). Alternatively, the centrifugal CD enables sample loading at the center of the disc, centrifugal transport through reaction chambers to the outer edge of the disc, and sample collection into small spots on the edge of the CD for MALDI-MS detection (refs 31,32). In addition, array-based technologies, such as the surface enhanced laser desorption ionization (SELDI) approach, have been shown to enable MALDI-MS detection from functionalized protein chips (ref 38).

Although the above microfluidic devices have demonstrated noteworthy sensitivity, throughput, and flexibility, they do not demonstrate the full benefits of microfluidic platforms combined with MS detection for a number of reasons. First, as mentioned, the main limitation of ESI-MS detection in the context of microfabricated analysis platforms relates to the traditionally sequential nature of the technique. This attribute inherently forfeits some of the greatest advantages provided by miniaturization, i.e., large-scale integration, multiplexing, and high-throughput analysis. Also, the fabrication of microfabricated ESI spray emitters is difficult, and their integration with microfluidic chips that perform complex sample processing steps has not been demonstrated. Second, the fabrication of piezo-actuated micro-dispensers that enable sample collection from multiplexed microfluidic chips for MALDI-MS detection is not simple, and their integration within sample processing chips has not been demonstrated either. Moreover, the dispensing process would deposit the sample onto a different chip than the one used for analysis, consequently increasing labor and costs. Third, the centrifugal CD does not enable the integration of a separation step prior to MS analysis since sample collection occurs in a single spot. Fourth, intense scrutiny of the SELDI chip approach has demonstrated that the technique is neither sufficiently reproducible, nor sensitive enough to detect low abundance signature biomarker components (ref 34). Also, the technique does not enable dynamic processing of biological samples as required for protein analysis.

Overall, microfluidic chips that enable complex sample processing followed by high throughput MS detection do not exist at the present time. For example, existing microfluidic devices may perform on-chip separation, but are subsequently connected to external pumping systems and autosamplers for MS detection. Such techniques do not provide sufficient throughput and cost-effective analysis. Therefore, what is needed is a small, microfluidic device comprising all the components necessary to perform complex sample separation as well as enable on-chip MS detection. Additionally, what is needed is a microfluidic device for complex sample processing that provides high sensitivity and throughput, requires only small amounts of complex samples, and minimizes overall analytical costs.

SUMMARY OF THE INVENTION

The present invention provides microfluidic devices and methods for on-chip complex sample processing. As disclosed herein, "device" refers to a platform or chip (e.g., microchip) for microfluidic analysis. "Complex sample" refers to any biological and/or chemical sample and may include samples such as tissue, blood, cerebrospinal fluid, saliva, urine, etc. The complex sample may comprise any number or combinations of substances, including, but not limited to, polyamino acids (e.g., peptides, polypeptides, proteins), polynucleotides (e.g., nucleic acids), sugars (e.g., polysaccharides), other biological and chemical macromolecules or complexes, and more simple substances, such as metabolic precursors and products, vitamins, co-factors, lipids, and other substances that can be found in environments comprising living organisms. Other non-limiting examples include organic compounds. Generally speaking, the device comprises several parts including: a separation channel of a complex sample separation system; an array of microreservoirs flanking the separation channel to one side; and an interface for transferring the separated sample components from the separation channel to the microreservoirs. According to one aspect, the interface serves to orthogonally transfer the separated components into the array of microreservoirs. In addition, the device may enable detection of separated components directly from the chip. Preferably, the device: 1) provides for the separation of a complex mixture into components; 2) orthogonally transfers the separated components into an array of microreservoirs via an interface; 3) enables on-chip detection of separated components; and/or 4) provides for multiplexed and/or parallel processing, thereby facilitating high-throughput investigations.

According to one embodiment, the device comprises a complex sample separation means, including at least a separation channel, for receiving a complex sample and separating it into components; and an interface means coupled to the separation means for orthogonally transferring the separated sample components into a collection means. In addition, at least the separation channel, interface means, and collection means are deposited within the same chip, facilitating analyte detection from the chip.

In general, the complex sample separation system functions to separate the sample based on various physical, chemical, and/or electrical properties (e.g., mass, size, charge, isoelectric point, hydrophobicity, affinity, etc.). At minimum, the separation system includes a separation channel. However, it may also include: various pumping components, eluent inlet and outlet reservoirs, mixing components, injecting components, and sample inlet and outlet channels. The operation of the separation channel may be based on pressure- and/or electrically-driven material transport mechanisms. Electrically-driven material transport mechanisms may be based on e.g., Electroosmotic Force or Electrokinetic Flow (EOF), and include application of sufficient voltage gradients via proximate electrodes disposed at both ends of the separation channel. Pressure-driven material transport mechanisms may be based on flow generated with a variety of pumping systems connected to the separation channel. In one exemplary embodiment, the separation system includes a high performance liquid chromatography (HPLC) system which is driven by a pump; however it is to be understood that other separation systems may also be used.

The interface operates to orthogonally transfer the separated sample components from the separation channel to the array of microreservoirs. Preferably, no separation takes place within the interface. According to one aspect, the interface simultaneously transfers the separated components to the microreservoirs. According to a further aspect, the interface controllably transfers the separated components to the microreservoirs. In yet a further aspect, the interface may be configured to operate as a valve and/or pump to controllably transfer the separated components. For example, the interface may be configured to operate as a valve (e.g., using EOF principles) to prevent leakage of the sample out of the separation channel.

According to an exemplary embodiment, the interface includes a plurality of microchannels that orthogonally intersect the separation channel at certain intervals. Flow through the microchannels may be controlled (i.e., induced or inhibited) using an electrically-driven material transport mechanism such as Electroosmotic Flow (EOF). In this embodiment, a plurality of electrodes may also be arranged adjacent the microchannels and activated with a sufficient voltage gradient to generate flow of sample components in a desired direction. Such electrodes may be embedded or inserted in the chip substrate, or externally arranged within the microreservoirs. Additionally, the microchannels preferably exhibit large hydraulic resistance to inhibit leakage of materials from the separation channel into the microchannels. Large hydraulic resistance may be obtained, for example, by providing very shallow and/or very narrow microchannels. According to one aspect, the depths of the microchannels within the substrate of the device may be less than 5 µm, and preferably between 0.1-3 µm. As a result of very small microchannels, EOF may thus be created by inducing flow through the microchannels (which act like small pores). As a voltage potential is applied across the microchannels, the interface may controllably elute the separated components from sections of the separation channel to the microreservoirs. In addition, it is to be appreciated that nanochannels may be used in the interface instead of microchannels to provide better separation resolution, etc.

In addition to the plurality of "eluting" microchannels (disposed between the separation channel and array of microreservoirs), the interface may also include a plurality of "rinsing" microchannels fluidly coupled to a rinse channel and disposed along an opposite side of the separation channel. The configuration of the rinsing microchannels may be such that they are aligned with the eluting microchannels on the other side of the separation channel. However, alternative configurations may be provided, for example, where the rinsing channels are staggered with respect to the eluting microchannels along the length of the separation channel.

In other various embodiments, the device may include a fully integrated sample separation system, array of microreservoirs, and interface that function as a stand-alone unit within the chip with no external assistance for fluidic propulsion. Alternatively, only the separation channel of the separation system is fully integrated into the chip while other components of the separation system are either fully or partially integrated. It is also to be understood that the above components may be disposed within a single substrate, between a plurality of substrates, or between a substrate and a cover plate of the chip. Moreover, the separation system and interface of the invention may include a multiplexed configuration within the microchip, thus even further improving high-throughput analysis.

According to yet another embodiment, innovative devices and methods for fast sample separation and transfer into a microarray configuration for direct detection (e.g., MALDI-MS) from the chip are provided. It is to be appreciated that current interfacing of separation systems to MALDI-MS is typically accomplished by sequential sample elution at the separation channel terminus and deposition into spots with the aid of a separate, external, piezo-dispenser, electrosprayer or a Probot instrument. In contrast to such techniques, the present invention advantageously provides: fast sample separation (e.g., by avoiding the need to wait for sequential elution of highly retained components); and parallel orthogonal sample collection into spots in the microreservoirs, thereby facilitating quicker arraying processes. In addition, by collecting the separated sample components in an array of microreservoirs, the present invention enables direct detection of separated components on the chip, and consequently faster analysis of separated sample components. For example, a snapshot MALDI-MS/MS image of the separated components may be provided, avoiding the need for an additional external device for microarray generation.

In another embodiment, the present invention enables off-line sample collection, processing and storage in the array of microreservoirs. Off-line processing facilitates convenient sample analysis at remotely-located MS labs, with no need for MS expertise at the collection site. The effective decoupling of the separation from MS detection facilitates operation of both techniques independently, at their own optimal speed dictated by the separation or MS performance. The capability to perform remote sample processing, decoupled from MS analysis, greatly advances the power of MS in the biological community and opens the possibility to more cost-effective sample processing. In addition, the chip can be stored and the sample reexamined again at a later time. Additionally, the chip may also be used to perform sample separation or fractionation alone, apart from MS analysis.

Advantageously, the present invention provides unique solutions to the implementation of microfluidic devices with MS detection, and advances entirely new approaches for designing analytical separations and interfaces to MS. The benefits of microfluidic manipulations reduce the overall surface areas that interact with the sample, thereby minimizing sample losses e.g., due to adsorption, and will become even more desirable as improvements continue to occur with respect to MS instrument sensitivity. In addition, the possibility of MALDI-MS/MS, an inherently high-throughput approach, will further spur the need for microfluidic multiplexed structures. The present invention is qualified to fill these roles.

BRIEF DESCRIPTION OF THE DRAWINGS

FIG. 11(A) shows an empty chip; FIG. 11(B) shows a chip filled with a fluorescent dye solution; FIG. 11(C) shows a chip that mimics the elution of the sample from the separation channel into the MALDI reservoirs (EOF is generated from left to right, as shown by arrow).

FIG. 12(A) shows a packed LC channel; FIG. 12(B) shows a channel loaded with a plug of fluorescent Rhodamine dye; FIG. 12(C) shows a channel after the elution of Rhodamine dye into the MALDI reservoir (no fluorescence).

DETAILED DESCRIPTION OF VARIOUS EMBODIMENTS

The present invention will now be described with respect to one or more particular embodiments of the invention. The following detailed description is provided to give the reader a better understanding of certain details of embodiments of the invention depicted in the figures, and is not intended as a limitation on the full scope of the invention, as broadly disclosed and claimed herein.

Figure 1A:
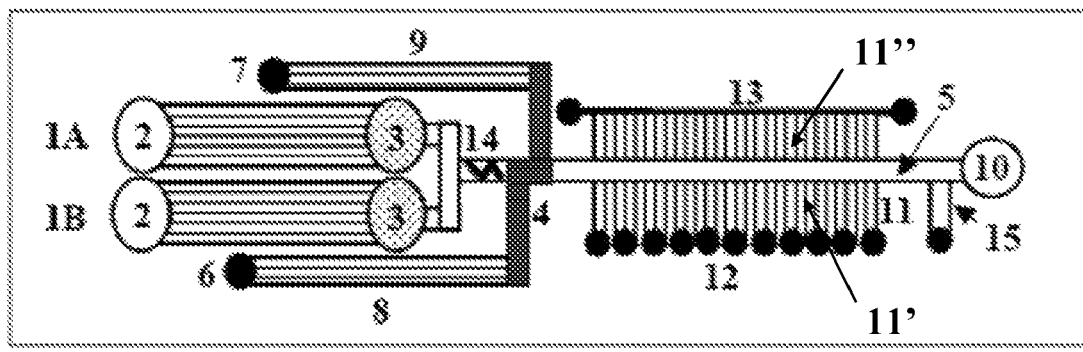
FIG. 1(A) illustrates an exemplary arrangement of the microfluidic device according to the principles of the present invention.

As an initial matter, it is instructive to see an illustrative embodiment depicting the microfluidic chip design in general. FIG. 1A shows a microchip integrated complex sample processing system including at least a separation channel (5) of e.g., a LC separation system, an (i.e., MALDI) interface (11) and array of microreservoirs (12). In this embodiment, the separation system comprises two pumps (1A, 1B), eluent inlet reservoir (2), eluent outlet reservoir (3), injector (4), separation channel (5), sample inlet reservoir (6), sample outlet reservoir (7) and mixer (14). All reservoirs contain electrodes (not shown) to enable the application of appropriate electrical fields for the operation of the chip. The electrodes can be embedded in the chip during the fabrication process, or inserted in the reservoirs later, during operation. The outlet reservoirs (3) contain a porous glass insert (not shown) to prevent EOF leakage into these reservoirs. The porous inserts enable exchange of ions but not of bulk flow. The inserts can be also embedded in the chip substrate, or inserted later and secured to the bottom of the reservoirs. It is to be understood. however, that other functional components may be included in the microfluidic design, as well. As shown in the Figure, the pumps (1A, 1B) are disposed side by side at one end of the chip. The pumps (1A, 1B) are composed of eluent inlet (2) and outlet (3) reservoirs fluidly connected by hundreds/thousands of micro/nanochannels. In one embodiment, the pumps (1A, 1B) may comprise EOF pumps with anywhere from 25-1000 micro/nanochannels. For example, the pumps (1A, 1B) may comprise 200 nanochannels approximately 2 cm long and 1.5 um deep that deliver the necessary flow rate and pressure. The outputs for both pumps (1A, 1B) are interfaced to a common mixer (14), e.g., a serpentine mixer, for combining the respective eluents. For example. a serpentine channel of 5-8 mm in length should suffice to ensure proper mixing of eluents within a few seconds. The mixer (14), in turn, exits directly to a double-T injector (4). One side of the double-T injector (4) is coupled to a sample reservoir (6) and the opposite side is coupled to a sample waste reservoir (7) via sample inlet (8), and outlet (9), channels respectively. In addition, the double-T injector (4) outputs to the separation channel (5) for separating the sample components. A waste reservoir (10) and side packing channel (15) are further located at the far end of the separation channel (5). As can be seen in FIG. 1A, the array of microreservoirs (12) flanks the separation channel (5) to one side, and the interface (11) fluidly couples sections of the separation channel (5) to the microreservoirs (12). According to one aspect, the interface (11) includes a plurality of eluting microchannels (11') between the separation channel (5) and the microreservoirs (12). In a further aspect, a rinsing channel (13) is longitudinally disposed along the opposite side of the separation channel (5) and is fluidly coupled to the separation channel (5) via a plurality of rinsing microchannels (11") which help to flush the separation channel contents out of the separation channel.

Pressurized fluid flows and eluent gradient capability may be created with the two multichannel EOF pumping systems (1A, 1B) and/or interface (11). The choice of an EOF pumping system to run the microfluidic device may be dictated by several considerations, including, but not limited to: 1) EOF pumps are the only miniaturized pumps that can generate high pressures (hundreds/thousands of bars); 2) the manufacturing of these pumps is extremely simple and reliable; 3) the same structure can be effectively utilized for sample loading and valving; and 4) the design facilitates stand-alone operation, multiplexing and high-throughput analysis. However, it is to be understood that the components on the chip that perform pumping, valving, mixing, preconcentration and separation, could be based on other principles of operation as well.

Figure 7:
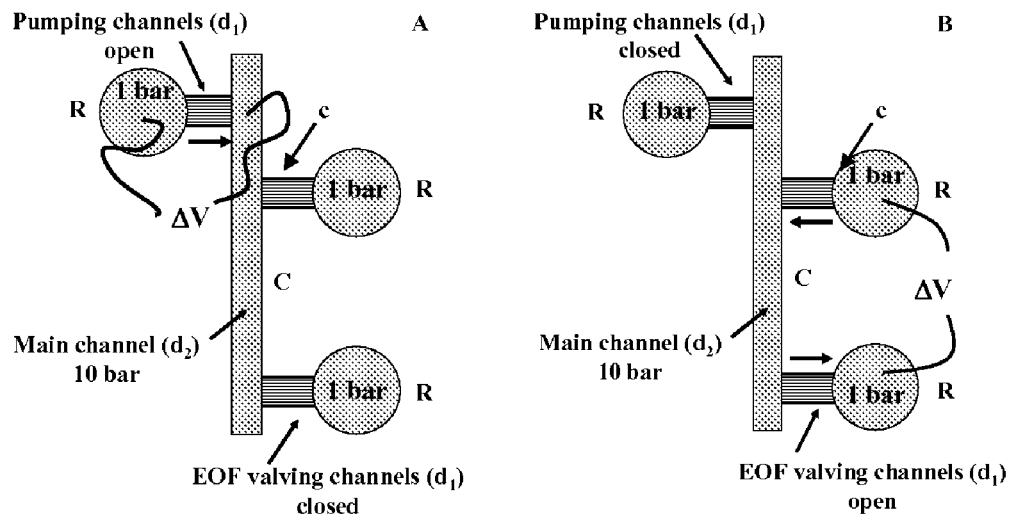
FIG. 7 is a schematic diagram that illustrates the pumping/valving principles of the present invention.

As mentioned, pumps (1A, 1B) may be comprised of hundreds/thousands of micro/nanochannels (i.e., approximately 0.1-2 μm in depth and about 2 cm long) that deliver the necessary flow and pressure. The amount of sample (not shown) that is loaded on the chip may be controlled by the number of channels, the time allowed for loading and proper channel dimensioning. Precise calculations for the pumping and valving systems allow for the generation of sufficient flow and pressure to accurately control the sample manipulations within the microfluidic network. For example, maximum operating pressures do not usually exceed 20 bars at flow rates of approximately 100-200 nl/min. These are typical operating parameters for nano-LC systems used in the last stages of proteomic investigations. It is understood, however, that higher or lower pressures may also be used. Detailed operation of the multichannel pumping/valving systems will be described later with respect to FIG. 7.

According to a preferred aspect, the separation channel (5) is relatively short. For example, the separation channel (5) may be approximately 2-4 cm, with a depth of approximately 50 μm. Prior to separation, reversed phase packing material with $d_p$=1-5 μm may be initially loaded in the channel (5) through a waste reservoir (10). The reversed phase packing material (e.g., Zorbax SB-C 18, $d_p$=5 μm, or another appropriate packing material) may be loaded in any suitable way (e.g., manually from the side channel (15) with a 250 μl syringe, a process performed very easily). After packing, the side channel (15) is typically (but not necessarily) plugged. It is appreciated that other separation channels are also possible, and include channels with coated walls and no packing within. Alternatively, other mechanisms of separation may be used altogether.

The microreservoirs (12) are approximately 0.8-1 mm in diameter and their depth determined by the width/thickness of the substrate (typically around 1.6 mm). According to one exemplary embodiment, the samples deposited in the microreservoirs may correspond to a plurality of MALDI "spots" such that component detection may take place directly from the chip. Depending upon the application, the microreservoirs may be implemented in glass substrates with even smaller thicknesses. Alternatively, other materials such as quartz, silicon, polymeric (organic or inorganic), ceramic, or any other material that facilitates manufacturing may be used. The above microreservoir (12) dimensions generally correspond to volumes of about 1.2 μl. In various embodiments, the microreservoirs (12) may be open to air, eluent evaporation could potentially occur during analysis. However, such eluent evaporation may be prevented by maintaining the microchip in an environment that is saturated with solvent vapor during operation.

The interface (11) preferably enables rapid collection of separated sample components into an array format for high-throughput analysis. For example, as a result of simultaneous parallel elution of sample components from the separation column (5), the separation time will typically be approximately 5-15 min, which is much shorter than typical LC analysis times (0.5-2 h) obtained with currently available instrumentation. As mentioned, shallow multichannel structures (hundreds/thousands of micro/nano-channels) with a large hydraulic resistance may be used to orthogonally transfer the sample from short sections of the separation channel (5) to the microreservoirs (12), under the influence of an electric field. Electrical contact to the microarrayed reservoirs (12) may be provided with the aid of a series of electrodes (not shown), such as, but not limited to, those comprising platinum, gold, silver, or other metals or alloys. The electrodes may be inserted or embedded within the substrate, or externally disposed, to achieve flow of the sample in the desired directions within the microfluidic device. Moreover, electric fields may be created with the aid of conventional external power supplies and controllers. The interface may include 10-1000 (or more) microchannels (11') approximately 0.1-2 μm deep and 5-20 mm long. The microchannels may couple each 0.5-2 mm section of the separation channel (5) to an approximately 0.8-1.0 mm reservoir (12). For example, the chips may comprise 2 cm long separation channels (5) flanked by 10-20 microreservoirs (12). Alternatively, 30-50, or more, microreservoirs may be used. In other words, it is possible that a single microreservoir (12) may correspond to one, or more, microchannels (11') depending upon the particular application, desired resolution, etc.

One topic worthy of discussion at this point concerns how the orthogonal sample transfer process relates to the preservation of separation integrity. In general, it will be appreciated that the larger the number of microreservoirs, the better the separation integrity and resolution will be preserved. Preferably, the number of microreservoirs should approach the peak capacity of a given separation channel. Currently, short LC columns used for proteomic applications rarely achieve a peak capacity of about $10^2$. However, peptide/protein samples can contain a much larger number of components. Thus, it is expected that each reservoir will collect several components (in excess of 20 components for very complex samples). This, however, will not represent a limitation of the MALDI-chip device. Most conventional nano-LC-ESI-MS systems that perform data dependent analysis are not capable of fully separating complex samples either, as 5-20 peptides are co-eluting most of the time. In addition, the separation channel length of the MALDI-chip could be adjusted (lengthened) according to the sample complexity to enable a better separation of all components. Prior to completing the separation, the escape of sample components from the separation channel (5) in the direction of the reservoirs (12) and channel (13), during the pressurized separation process, will be prevented, for example by two factors. First, the microchannels exhibit large hydraulic resistance, which helps to prevent bulk flow leakage from channel (5). Second, an extremely small electroosmotic counter-flow, from reservoirs (12) and channel (13) in the direction of the separation channel (5) may be maintained during the entire length of the separation process.

When the separation in the main channel (5) is completed, the EOF pumps (1A, 1B) are turned off, and a potential differential (approximately 100-200 V/cm) is applied across the separation channel (5) via the interface (11), for example between channel (13) and each microreservoir (12). The contents of channel (5) are transferred to reservoirs (12) through an electroosmotic mechanism and/or with the aid of eluent coming from the rinse channel (13). The total dead volume of the separation channel (5) is estimated to be less than 0.5 ul, and is flushed out with approximately 5-10 μl of eluent from rinse channel (13), i.e., 10 times the volume of the empty section of the column. Sufficient time should be allowed for this process to prevent sample hold back in the separation channel (5); however, it is typical that the transfer will be complete in less than about 5 min. In addition, the solution for sample transfer through the nanochannels (11') is preferably high in organic content (e.g., up to 80-90% methanol or acetonitrile) to prevent sample losses due to adsorption on the nanochannel walls.

Figure 1B:
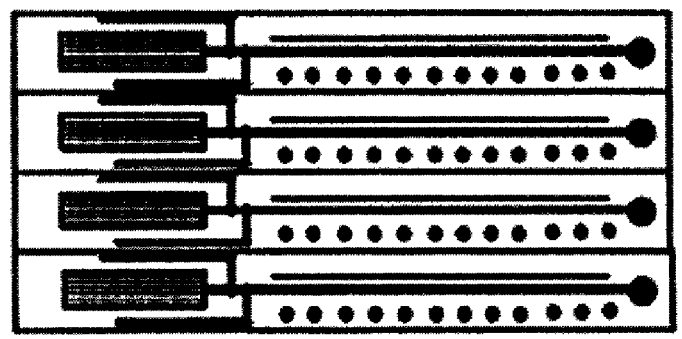
FIG. 1(B) illustrates an exemplary multiplexed configuration of the arrangement of FIG. 1A.

As shown in FIG. 1B, the microchip configuration may be replicated 2-4, or more, times to result in a disposable, high-throughput multiplexed platform. Although the Figure shows four processing lines on the chip, use of various fabrication techniques such as reactive ion etching will enable the fabrication of high-aspect ratio, high-density structures, that result in more extensive multiplexing capabilities. Advantageously, multiplexed structures provide improved sensitivity, inter-channel and inter-chip reproducibility, and applicability for high-throughput applications. Moreover, the chips may further be disposable and prone for single-use analysis, or may be reusable.

Figure 2:
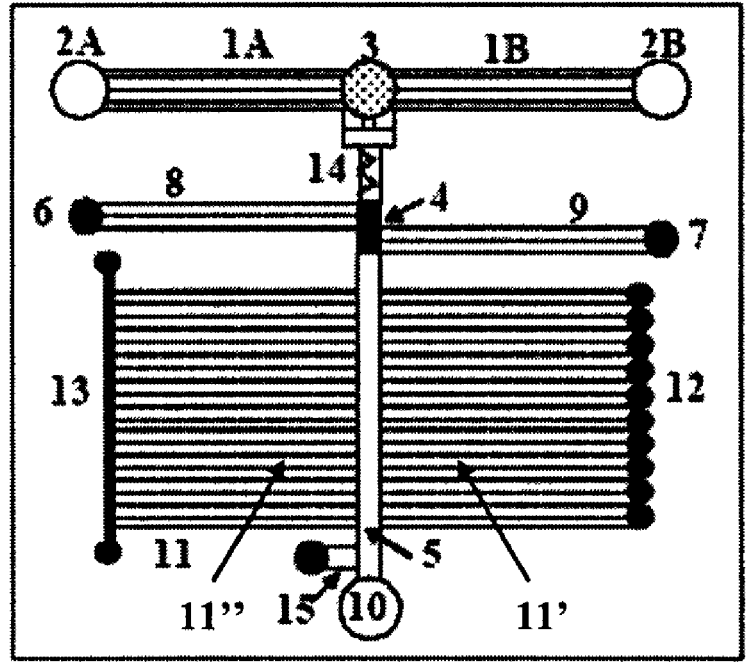
FIG. 2 illustrates another exemplary embodiment of the microfluidic device according to the principles of the present invention.
Figure 3:
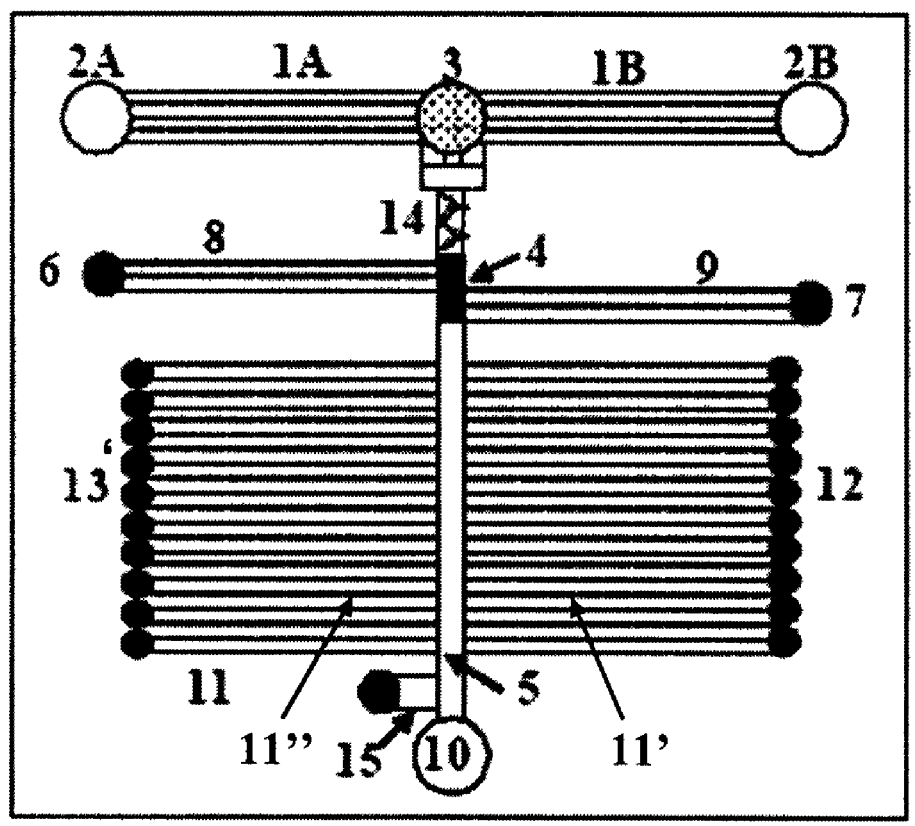
FIG. 3 shows an alternative embodiment comprising an array of reservoirs (13') instead of rinse channel (13).
Figure 4:
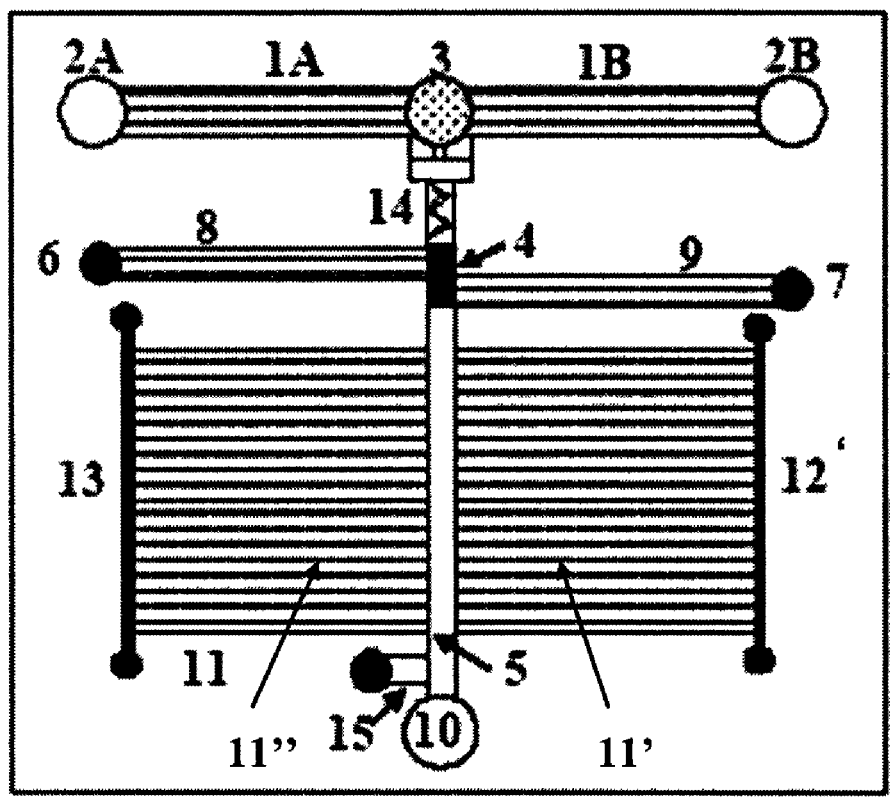
FIG. 4 shows another embodiment comprising a common channel (12') instead of an array of microreservoirs (12).
Figure 5:
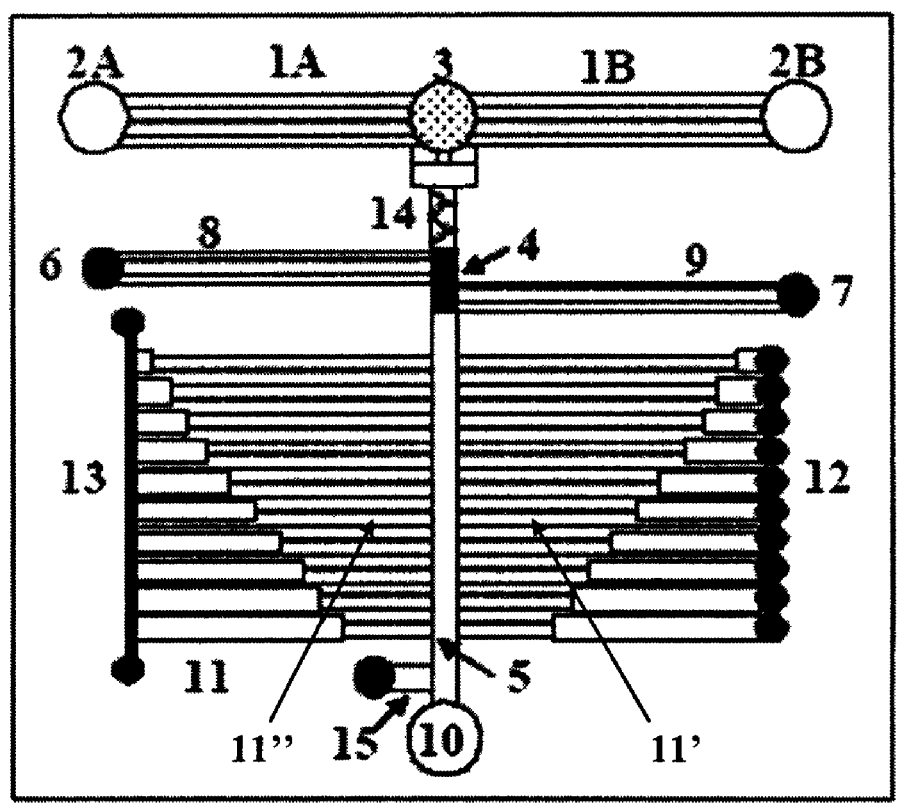
FIG. 5 illustrates yet another embodiment wherein the depths of microchannels (11') and/or (11") vary along the length of the separation channel (5).

FIG. 2 shows another possible configuration of the components on the chip. In this embodiment, the pumps (1A, 1B) are collinearly disposed and share a common outlet reservoir (3) between them. In other words, the microchannels and inlet reservoirs (2A, 2B) are oppositely disposed along a (common axis). As in FIG. 1, the contents of the two pumps (1A, 1B) are output to a mixer (14). However, eluent inlet (6) and outlet (7) reservoirs and channels (8) and (9), respectively, are also collinearly disposed on opposite sides of the injector (4). As indicated by the Figures, it is to be understood that various combinations and configurations of the components on the chip may be implemented according to the desired application, chip fabrication technique, multiplexed arrangement on the chip, etc. In addition, to demonstrate various other possible sample manipulation and detection embodiments, FIG. 3 illustrates where the rinse channel (13) may be replaced by an array of reservoirs (13'). Additionally or alternatively, FIG. 4 illustrates where the array of reservoirs (12), in turn, may be replaced by a common channel (12'). In this Figure, one or more microchannels (11') elute into a single channel, however it is understood that in other embodiments, the microchannels (11') may each elute into a single corresponding reservoir (12), or one or more microchannels (11') into one reservoir, etc. Furthermore, FIG. 5 illustrates another embodiment where the lengths of the individual microchannels (11') vary to compensate for pressure differentials that may be encountered along the separation channel (5) and/or leakage at the channel head. As can be seen in the Figure, the lengths of the microchannels (11'), (11") vary such that they are longer at the channel head where pressure is high, and shorter at the channel end where pressure is low. The very wide channels correspond to conventional low hydraulic resistance elements which are fluidly coupled to the large hydraulic resistance microchannels (11',11"). Alternatively, instead of varying the length of the interface microchannels, another approach toward compensating for pressure differentials in the separation channel may be to increase the field strength across the separation channel at the beginning relative to its end, such that stronger EOF compensates for leaks at the channel head, etc. This will be accomplished with properly positioned electrodes along the length of the separation channel.

Figure 6:
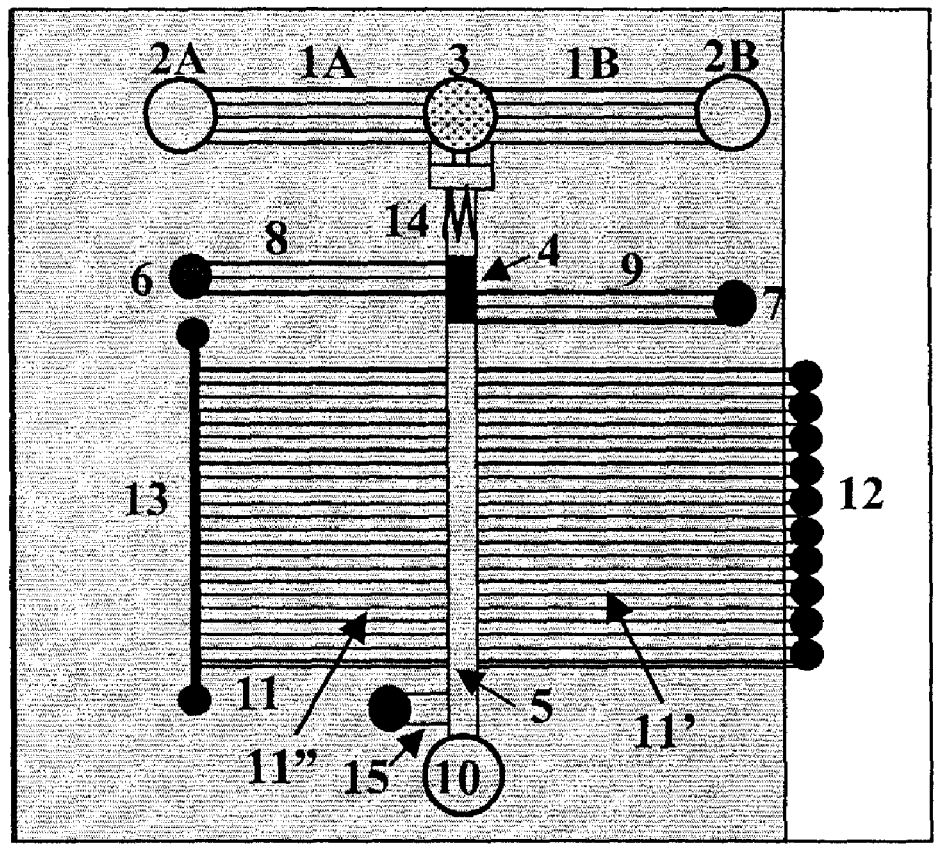
FIG. 6 shows another embodiment with exposed microreservoirs (12).

FIG. 6 shows an embodiment where the microreservoirs (12) are fully exposed (e.g., to air). In this particular embodiment, the microreservoirs (12) are relatively shallow and fabricated directly into the surface of the substrate. Such a configuration provides the possibility to directly access the sample components contained in the microreservoirs (12) for ionization, detection, manipulation, removal, etc. For example, it may be advantageous to provide open reservoirs (12) for direct laser access for sample ionization and/or detection. In addition, it is to be understood that the shape of the microreservoirs (12) may comprise any suitable shape advantageous for sample storage, removal, manipulation, detection, etc. It is to be appreciated that the shape may also depend upon the fabrication technique used. Likewise, it is to be understood that the cross-section of the micro/nano-channels as well may vary according to the intended application, fabrication technique used, etc. Suitable microreservoir shapes and/or microchannel cross-sections include circular, semi-circular, oval, square, rectangular, or other various shapes.

The microfluidic devices are preferably fabricated of glass, however other materials such as quartz, polymeric- or silicon-substrates, or the like, may be used. In an exemplary embodiment, glass was chosen for several reasons: it is optically transparent and fluidic manipulations can be visualized with a fluorescent microscope; it is able to withstand high pressures, it is a good electrical insulator; EOF is easily generated in glass; and, the surface chemistries are well known. Glass substrates, coated with chrome and positive photoresist, and photomasks may be purchased from various manufacturers. In addition, the microfluidic layout of the photomask may be prepared and easily redesigned with AutoCAD software. Such microchips may be fabricated according to conventional techniques (9): alignment of the substrate and photomask, exposure to UV light (360 nm), developing/removal of the irradiated photoresist, selective removal of the chrome layer, wet chemical etching of channels in glass, removal of the remaining chrome layer, drilling access holes in the cover plate, cleaning with detergent, acetone and methanol, hydrolysis/activation of the microchip surface, and thermal bonding of the substrate to the cover plate by gradual heating to 550° C. Glass reservoirs (approximately 10 ul) may be bonded to the cover plate, and electrical contact to the reservoirs provided with platinum electrodes and computer-controlled power supplies. In general, suitable techniques and materials are available in the art to fabricate any embodiment of the device of the invention, given the design and general method of use described herein.

An exemplary protocol for sample manipulation on the chip will now be provided. At the start of the analysis, the entire system is filled with e.g., an LC eluent (not shown). The sample is placed in sample reservoir (6), and loaded/preconcentrated in the double-T injector (4) by applying a potential differential (approximately 500 V/cm) between reservoirs (6) and (7). After loading, the potential differential between reservoirs (6) and (7) is removed, and pumps (1A, 1B) are activated by applying a potential differential between reservoirs (2) and (3). The field strength on pumps (1A, 1B) is in the 500-1,000 V/cm range, and may be adjusted to provide for sufficient flow through the separation channel (5). Initially, eluent will be collected in a large waste reservoir (10) placed at the end of the separation channel (5). This eluent volume is approximately equivalent to the dead volume of the separation channel (5). Next, separation is performed. The composition of the separation eluent and the gradient elution of the analytes may be optimized such that once the separation is completed, the sample components are distributed uniformly along the length of the separation channel (5). At the time the first components reach the end of the channel (5), the last eluting components are reaching the beginning. The eluent will typically be pH stabilized with adequate buffers. A relatively shallow gradient should be sufficient to complete the separation, as most peptides elute within a range of 10-35% acetonitrile content in the eluent. After the completion of the separation, the electrical field to the pumps (1A, 1B) is turned off. The transfer of the separation channel (5) content to the microarray of reservoirs (12) occurs at this stage of analysis by applying a potential differential between channel (13) and the microarray of reservoirs (12). The content of each section of the separation channel (5) is transferred e.g., electroosmotically, through a set of fine microchannels (11'), to corresponding microreservoir(s) (12).

According to an exemplary embodiment interfaced with MALDI-MS, once the separated components are collected in the microarray of reservoirs (12), the solvent is evaporated under a gentle stream of gas, such as nitrogen gas, to allow for the deposition of the sample on the bottom of the microreservoirs (12). This process may be optimized to avoid sample losses on the reservoir sides. If the latter occurs, some of the sample may be recuperated by dissolution during the addition of matrix solution, which typically contains 50% acetonitrile. However, the relative ratio of the reservoir side-area to its bottom-area is small, and significant sample losses are not expected to occur under normal use. In addition, to prevent sample diffusion back to the separation channel (5), a very small flow of eluent from channel (13) to reservoirs (12), may be maintained during the evaporation process. Next, a MALDI matrix (e.g., α-cyano-4-hydroxycinnamic acid) may be added to each reservoir by any suitable technique, such as, but not limited to, pipetting or by flooding the chip surface with the matrix solution (provided that contamination is avoided), etc. The volume of the microreservoirs (12) (approximately 1 μl) corresponds to typical sample volumes that are commonly applied to commercial MALDI plates. In this embodiment, however, the samples remaining in the microreservoirs correspond to a plurality of MALDI spots, whereby MS detection may take place directly from the chip.

The escape of the sample components from the separation channel (5) in the direction of the reservoirs (12) and channel (13) during loading, separation, etc. may be prevented by at least the following two factors. First, the large hydraulic resistance of the microchannels (11'), (11") during valving operation prevents bulk flow leakage from separation channel (5). Additionally, or alternatively, an extremely small electroosmotic counter-flow from reservoirs (12) and channel (13) in the direction of the separating channel (5) may be maintained during the entire length of the separation process. When separation is complete, the eluting microchannels (11') (and rinsing channels (11")) may be used as a pump for transferring the content of the separation channel (5) into the microreservoirs (12). In addition, the rinsing channel (13) may be used to flush the separated components out of the separation channel (5). The volume of rinsing fluid volume may be calculated to be at least 5 times larger then the corresponding empty section of the channel (which for a packed channel would correspond to more than 10 times the void volume of that column section). This will ensure that no sample is lost due to retention in the column as a result of transfer to the channels (11'), or due to adsorption on the microchannel walls.

FIG. 7A provides a detailed illustration of the pumping and/or valving capabilities of the microchannel configurations. Consider a main channel (C) with diameter $d_2$ that is connected to a few reservoirs (R) through a series of shallow microchannels (c) with diameter $d_1$. If a potential differential (ΔV) is applied between a reservoir (R) and the main channel (C), EOF will be generated through the connecting microchannels (c); if the hydraulic resistance of these microchannels (c) is sufficiently high, eluent will be pumped from the reservoir (R) into channel (c) even if the channel is pressurized, e.g., at 10 bar. The large hydraulic resistance of the pumping microchannels (c) will impede flow leakage back into the reservoir (R). The microchannels (c) may be approximately 1-2 um deep and 5-20 mm long, and capable of delivering flow rates in the 10-400 nl/min range; however, other configurations may be used. A valving structure comprised of similar narrow microchannels (c) as the ones used for pumping can be used for injecting and processing the sample in a pressurized environment. As the multiple open channel configuration has a much larger hydraulic resistance than any of the other functional elements on the chip, it can basically act as a valve that is open to material transport through an electrically driven mechanism, but is closed to material transport through a pressure driven mechanism. The same multichannel structure can be used as an EOF pump for eluents, and as an EOF valve for sample introduction into a pressurized microfluidic system. If the depth of the microchannels (c) is small enough, the hydraulic resistance is so large that one set of microchannels (c) can be used for pumping, and several other sets for valving (FIG. 7B). Sample will be introduced and removed from the main channel (C) on the chip only when a potential differential is applied between adequate sample reservoirs (R), at appropriate moments during the analysis. When the sample introduction/waste channels (not shown) are of similar size to the pumping microchannels (c), the pressure driven fluid loss through these channels is negligible. If $d_1/d_2$ is approximately 0.01, the pumping microchannels (c) can deliver fluid flow effectively even through a large hydraulic resistance element such as channel (C), with minimal loss of flow through the non-pumping/valving channels. For example, consider a simplified model that comprises the same number of microchannels (c) involved in pumping and valving, and all pumping and valving channels have diameter $d_1$ and length $L_1$. The main channel on the chip, say the separation channel (C), has diameter $d_2$, but is 1000 times longer then the pumping/valving channels ($L_2=1000 \times L_1$). For the simplicity of the model, we have considered an extremely long separation channel (C) that would have a similar hydraulic resistance as a short, packed channel. For $d_1/d_2=0.01$, the ratio between the pressurized flow in the main channel and the EOF generated by the pumping microchannels, will be almost equal to 1, and will be essentially unaffected by the additional injection/waste channels that do not pump. This means that the electroosmotic flow will not leak out through these valving channels. The pressurized flow would drop to only 90% of the original EOF when $d_1/d_2=0.02$, and to 50% when $d_1/d_2=0.1$ ($L_1:L_2=1:1000$ in both cases). Consequently, a configuration with appropriate dimensions can be used for pumping and valving, and thus for implementing a separation system, such as an HPLC system, on a microchip.

Figure 8:
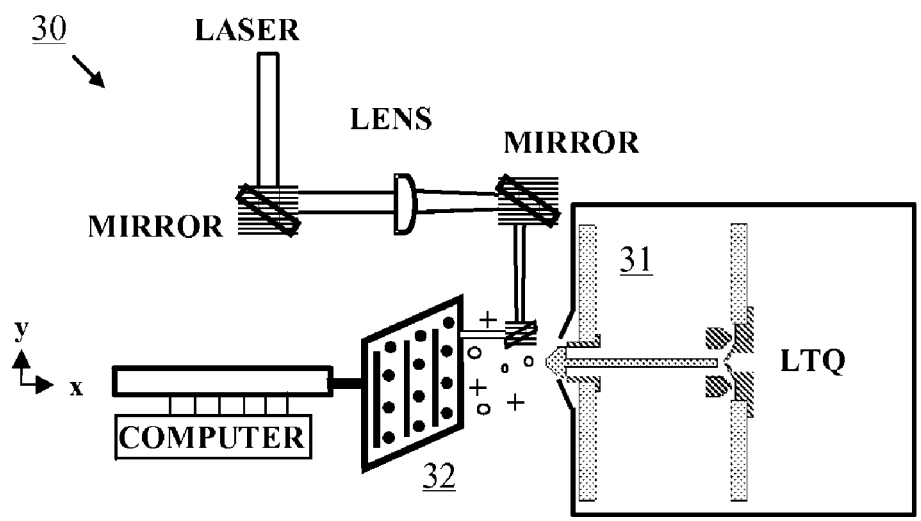
FIG. 8 shows an exemplary microchip according to the principles of the present invention interfaced with a component detection system.
Figure 9:
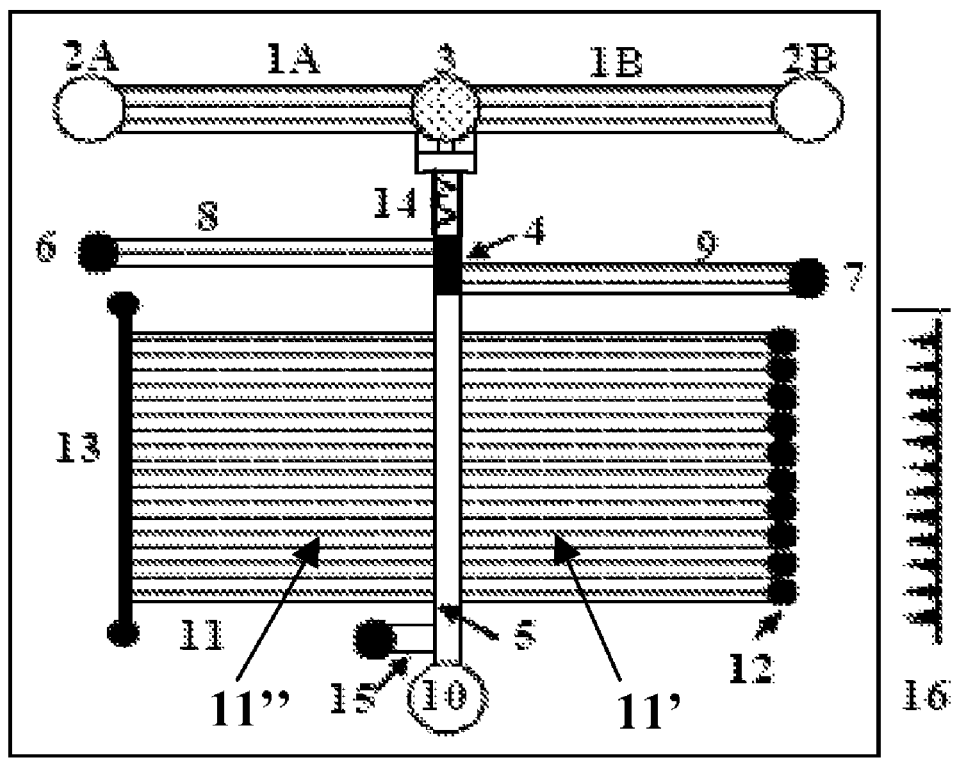
FIG. 9 shows an exemplary microchip according to the principles of the present invention interfaced with a sample removal device (16).

As depicted in FIG. 8, an AP-MALDI source (30) may be interfaced with a conventional mass spectrometer (31) for sample detection directly from a microchip (32) of the present invention. The AP-MALDI source (30) may generally consist of a (e.g., nitrogen) laser for sample ionization (337 nm), a computer-controlled XYZ stage to align the chip (32) (and specific sample spots) with the sampling orifice of the mass spectrometer (31), and various conventional optical components to direct and focus the laser beam onto the sample spots. The size of the beam may be adjusted to generate maximum signal intensity. The micro-arrayed chip (32) is placed in sufficiently close proximity to the mass spectrometer (31) inlet. Data may be typically collected at 5-10 Hz (or more) with the aid of commercial software provided for the MS instrument (31). The XYZ stage and power supplies that operate the chip (32) may be computer-controlled using, for example, LabView software and computer boards purchased from National Instruments. The MS acquisition method may be configured to generate for each spot a high quality MS spectrum followed by e.g., 5-10 MS/MS spectral acquisition steps on the most intense peaks that were identified in the MS spectrum. Although an AP-MALDI source (30) is depicted in this figure by way of example, it is understood that the device may also be interfaced with subatmospheric MALDI, surface enhanced laser desorption ionization (SELDI), desorption/ ionization on silicon (DIOS), laser desorption, or other MS source. According to various embodiments, the device may also be interfaced with any appropriate component detection system such as an optical detection system, such as a fluorescence detection system, CCD arrays, etc. As shown in FIG. 9, the device may additionally be interfaced with a component removal system (16) (such as, but not limited to, an electronic pipettor) for removal of the samples for subsequent analysis by another instrument and method.

Figure 10:
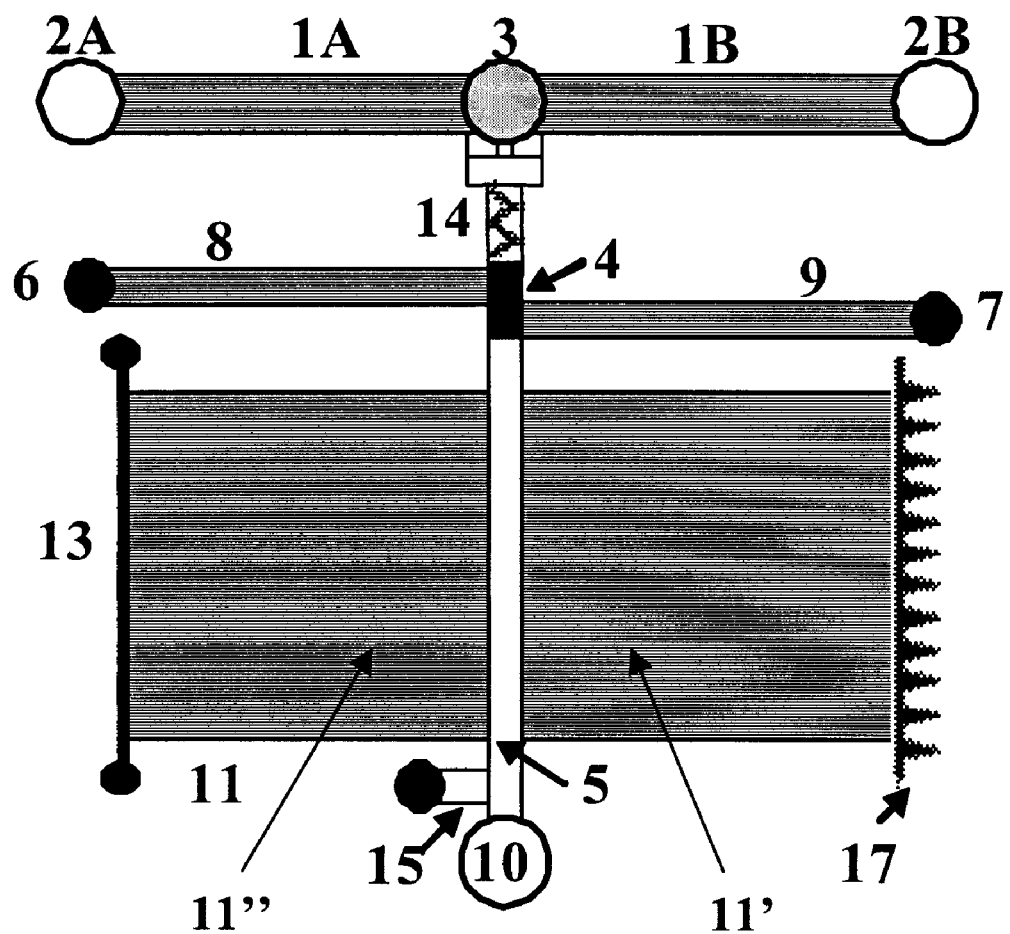
FIG. 10 illustrates an alternative embodiment wherein microchannels (11') are interfaced with micro/nano-channel spray emitter(s) for ESI-MS analysis.

In other various works, the inventor has developed a fully integrated LC-ESI system on a chip (refs 35-37). The configuration of the devices consist of stand-alone components that occupy an area of only a few square centimeters. While the mechanism of operation relies on electroosmotic pumping principles, the devices enable stable flow generation in electrical field free regions of a chip, a feature that is necessary for the implementation of pressure driven processes. Operational flow ranges are consistent with the requirements of conventional nano-LC systems. Although compact, these devices, however, do not address the complexities of high-throughput sample analysis. The embodiment of FIG. 10 invention applies to high-throughput ESI-MS and illustrates an exemplary embodiment wherein the microchannels (11') are interfaced with micro/nano-channel spray emitter(s) (17). By interfacing a plurality of spray emitters at the end of the microchannels (11'), the separated sample components may be processed simultaneously in parallel, thereby increasing the overall speed of ESI-MS analysis.

According to an exemplary aspect, biomarker detection and protein co-expression profiling may be performed with the devices and methods of the invention. Although differential protein expression profiling for the discovery of novel biomarkers is beyond this disclosure, the demonstration of this technology for confident identification of a set of pre-established target proteins (that could be potentially used for high-specificity screening applications) is proposed. For this purpose, the operation of the chips may be optimized to enable preferential high-resolution separation and identification of peptides that match specific biomarker proteins. Typical peptide fractions submitted to LC-MS analysis may contain up to 200-500 components (ref 38). A microchip (32) with a 2 cm separation channel flanked by approximately 10-20 microreservoirs would collect theoretically 10-50 peptides in each reservoir. This should not cause any problems, as in the case of flowing LC with ESI-MS/MS detection, several peaks are coeluting almost all the time. With benchtop LC-MS runs where the active separation time was less than 15 min, it was possible to confidently identify over 100 proteins matched by more than 200 peptides. The mass spectrometer (31) was configured to acquire for each MS spectrum, on the fly, 5 $MS^2$ spectra on the most intense peaks. The time allowed for these investigations was consequently limited by the chromatographic peak width (15-30 s), which may be very short for a thorough $MS^2$ exploration. However, an LC-MALDI-chip should eliminate these problems as the static arrangement would enable sufficient time for MS/MS data collection from each MALDI reservoir (12). Furthermore, MS/MS data may be acquired from each reservoir using conventional ESI-MS/MS equipment and subsequently interpreted in any suitable fashion, for example by the Sequest algorithm.

EXAMPLE

The invention will now be further explained through an example of an embodiment and configuration. The example, like the detailed description above, is included solely to provide an individual example of an embodiment, and are not to be interpreted as a limitation of the invention as broadly disclosed and claimed herein.

Example 1

Microfluidic LC-MALDI Chips

Figure 11:
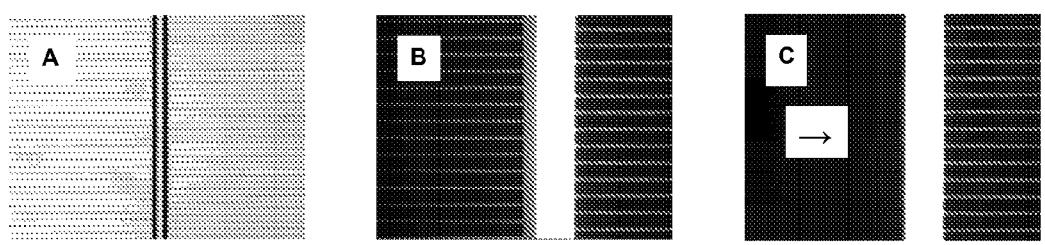
FIG. 11 shows an enlarged area of a microfluidic LC chip interfaced through a series of nanochannels to MALDI collection reservoirs.

The first generation of microfluidic-MALDI chips was constructed and tested with fluorescent dyes. A region of an empty separation channel that is intersected by a multitude of 1.5 µm deep channels for MALDI sample collection is shown in FIG. 11A. In the present design, there are 10 microreservoirs for sample collection, the intersecting nanochannels are placed 50 µm apart, and each 2 mm section of the LC separation channel is connected through 40 nanochannels to a sample collection reservoir. Alternative designs may incorporate a large density of nanochannels that enable the connection of sub-millimeter separation channel regions to the MALDI reservoirs. FIG. 11B shows the microfluidic chip filled with a fluorescent dye. The elution of the LC separation channel content through the intersecting nanochannels into the MALDI reservoirs is shown in FIG. 11C. The chip was filled with a fluorescent dye solution and the sample rinse channel and collection reservoirs were filled with blank eluent; EOF was generated from left to right, and as a result of the blank eluent flowing into the separation channel, the left side nanochannels are dark and not visible in the figure. The right side nanochannels still contain fluorescent dye coming from the separation channel, and are bright and visible.

Figure 12:
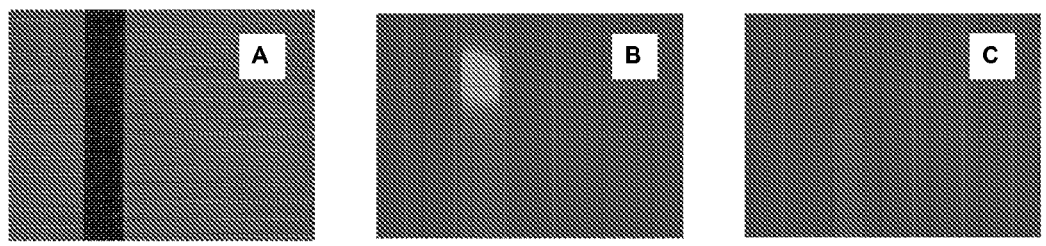
FIG. 12 depicts a fluorescent image showing a section of the separation channel from the microfluidic LC-MALDI-MS chip.
Figure 13:
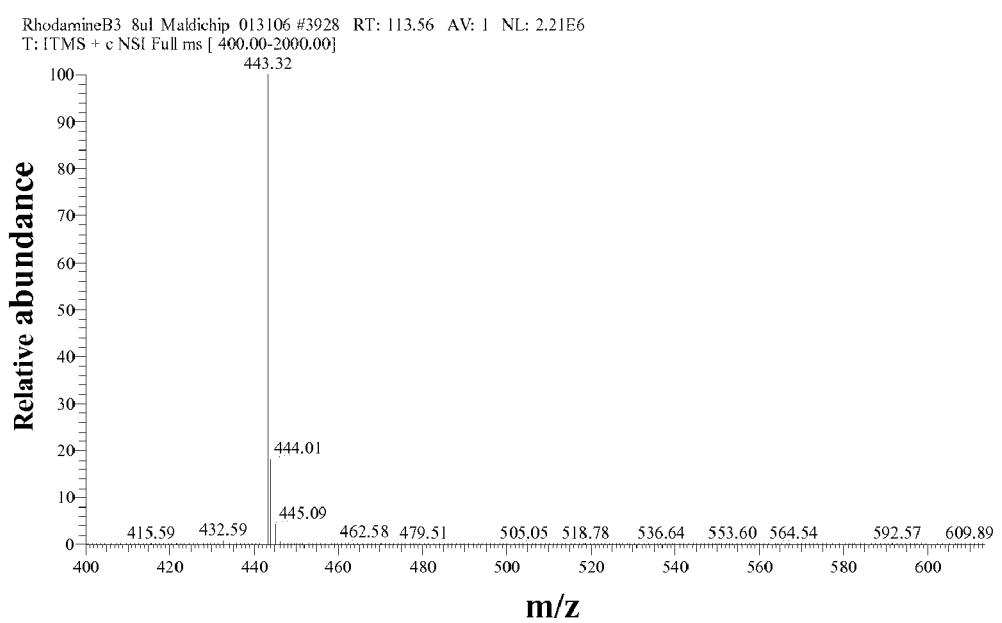
FIG. 13 shows a mass spectrum of Rhodamine 610 fluorescent dye collected from one of the microarray reservoirs.

One LC-MALDI chip that had its separation channel filled with packing material (FIG. 12A), was manually loaded with concentrated Rhodamine fluorescent dye solution, to visualize the capability to handle the sample within the packed channel, to elute it from the packing material, and to collect it in a MALDI reservoir. A section of the packed LC channel (5) loaded with Rhodamine 610 is shown in FIG. 12B (see bright spot in the packed channel). The same section, after Rhodamine 610 elution from the channel into the MALDI reservoir, is shown in FIG. 12C (the channel does not contain any more fluorescent dye, and is dark). A mass spectrum of Rhodamine 610 is shown in FIG. 13, and demonstrates that the sample can be efficiently collected in these MALDI reservoirs for further detection.

While various preferred embodiments have been shown and described, it will be understood that there is no intent to limit the invention by such disclosure. Other modifications may include, but are not limited to: increasing sample loading capacity by increasing the number of loading microchannels (proportionally increasing the density of the micro/nanochannels as well), or by increasing the field strength. Additionally, the use of various techniques for etching, e.g., reactive ion etching techniques, that enable the fabrication of high-aspect ratio, high-density structures, may be employed that will result in more extensive multiplexing capabilities. Advantageously, the device enables off-line sample collection, processing and storage into an array which facilitates convenient sample analysis at remotely-located labs at a later time. Because the separation is decoupled from MS detection, both techniques may be performed independently. For example, separation or fractionation alone may be performed with the device without MS analysis. In addition, the disclosure is intended to cover all modifications and alternative constructions falling within the spirit and scope of the invention as defined in the appended claims.

REFERENCES

The following references are cited and discussed above. Each reference is incorporated herein in its entirety.
1. M. R. Larsen; P. Roepstorff, Mass spectrometric identification of proteins and characterization of their post-translational modifications in proteome analysis, *Fresenius J. Anal. Chem.* 2000, 366, 677-690.
2. D. A. Wolters, M. P. Washburn; J. R. Yates, III, An automated multidimensional identification technology for shotgun proteomics, *Anal. Chem.* 2001, 73, 5683-5690.
3. V. L. Laiko; S. C. Moyer; R. J. Cotter, Atmospheric pressure MALDI/ion trap mass spectrometry, *Anal. Chem.* 2000, 72, 5239-5243.
4. M. C. Galicia; A. Vertes; J. H. Callahan, Atmospheric pressure matrix-assisted laser desorption/ionization in transmission geometry, *Anal. Chem.* 2002, 74, 1891-1895.
5. C. A. Miller; D. Yi; P. D. Perkins, An atmospheric pressure matrix-assisted laser desorption/ionization ion trap with enhanced sensitivity, *Rapid Commun. Mass Spectrom.* 2003, 17, 860-868.
6. S. C. Jakeway; A. J. De Mello; E. L. Russell, Miniaturized total analysis systems for biological analysis, *Fresenius J. Anal. Chem.* 2000, 366, 525-539.
7. P. A. Greenwood, G. M. Greenway, Sample manipulation in micro total analytical systems, *Trends in Anal. Chem.* 2002, 21(11), 726-740.
8. D. Boone; Z. H. Fan; H. H. Hooper; A. J. Ricco; H. Tan; S. J. Williams, Plastic microfluidic devices, *Anal. Chem.* 2002, February, 78A-86A.
9. S. C. Jacobson; T. C. Culbertson; J. E. Daler; J. M. Ramsey, Microchip structures for submillisecond electrophoresis, *Anal. Chem.* 1998, 70, 3476-3480.
10. Q. Xue; F. Foret; Y. M. Dunayevskiy; P. M. Zavracky; N. E. McGruer; B. L. Karger, Multichannel microchip electrospray mass spectrometry, *Anal Chem.* 1997, 69, 426-430.
11. R. S. Ramsey; J. M. Ramsey, Generating electrospray from microchip devices using electroosmotic pumping, *Anal Chem.* 1997, 69, 1174-1178.
12. Q. Xue; Y. M. Dunayevskiy; F. Foret; B. L. Karger, Integrated multichannel microchip electrospray ionization mass spectrometry: analysis of peptides from on-chip tryptic digestion of mellitin, *Rapid Commun. Mass Spectrom.* 1997, 11, 1253-1256.
13. D. Figeys; Y. Ning; R. Aebersold, A microfabricated device for rapid protein identification by microelectrospray ion trap mass spectrometry, *Anal Chem.* 1997, 69, 3153-3160.
14. D. Figeys; S. P. Gygi; G. McKinnon; R. Aebersold, An integrated microfluidics-tandem mass spectrometry system for automated protein analysis, *Anal Chem.* 1998, 70, 3728-3734.
15. N. Xu; Y. Lin; S. A. Hofstadler; D. Matson; C. J. Call; R. D. Smith, A microfabricated dialysis device for sample cleanup in electrospray ionization mass spectrometry, *Anal Chem.* 1998, 70, 3553-3556.
16. J. Li; P. Thibault; N. H. Bings; C. D. Skinner; C. Wang; C. L. Colyer; D. J. Harrison, integration of microfabricated devices to capillary electrophoresis-electrospray mass spectrometry using low dead volume connection: application to rapid analyses of proteolytic digests, *Anal Chem.* 1999, 71, 3036-3045.
17. I. M. Lazar; S. A. Sundberg; R. S. Ramsey; J. M. Ramsey, Subattomole-sensitivity microchip nanoelectrospray source with time-of-flight mass spectrometry detection, *Anal. Chem.* 1999, 71, 3627-3631.
18. I. M. Lazar; R. S. Ramsey; S. C. Jacobson; R. S. Foote; J. M. Ramsey, Novel microfabricated device for electrokinetically induced pressure flow and electrospray ionization mass spectrometry, *J. Chromatogr. A* 2000, 892, 195-201.
19. G. A. Schultz; T. N. Corso; S. J. Prosser; S. Zhang, A fully integrated monolithic microchip electrospray device for mass spectrometry, *Anal. Chem.* 2000, 72, 4058-4063.
20. J. Kameoka, R. Orth, B. Ilic; D. Czaplewski; T. Wachs; H. G. Craighead, An electrospray ionization source for integration with microfluidics, *Anal. Chem.* 2002, 74, 5897-5901.
21. J. Sjödahl, J. Melin; P. Griss; Å. Emmer; G. Stemme, J. Roeraade, Characterization of micromachined hollow tips for two-dimensional nanoelectrospray mass spectrometry, *Rapid Commun Mass Spectrom.* 2003, 17, 337-341.
22. C. A. Keetch; H. Hernandez; A. Sterling; M. Baumert; M. H. Allen; C. V. Robinson, Use of a Microchip Device Coupled with Mass Spectrometry for Ligand Screening of a Multi-Protein Target, *Anal. Chem.* 2003, 75, 4937-4941.
23. Y. Deng; J. Henion; J. Li, P. Thibault; C. Wang; D. J. Harrison, Chip-based capillary electrophoresis/mass spectrometry determination off carnitines in human urine, *Anal. Chem.* 2001, 73, 639-646.
24. S. Ekström; D. Ericsson; P. Önnerfjord; M. Bengtsson; J. Nilsson; G. Marko-Varga; T. Laurell, Signal amplification using "spot-on-a-chip" technology for the identification of proteins via MALDI-TOF MS, *Anal. Chem.* 2001, 73, 214-219.
25. T. Miliotis; S. Kjellström; J. Nilsson; T. Laurell; L. E. Edholm; G. Marko-Varga, Capillary liquid chromatography interfaced to MALDI-MS using on-line coupled piezoelectric flow-through microdispenser, *J. Mass Spectrom.* 2000, 35, 369-377.
26. J. Liu; K. Tseng; B. Garcia; C. B. Lebrilla; E. Mukerjee; S. Collins; R. Smith, Electrophoresis separation in open microchannels. A method for coupling electrophoresis with MALDI-MS. *Anal. Chem.* 2001, 73, 2147-2151.
27. J. Li; T. LeRiche; T.-L. Tremblay; C. Wang; E. Bonneil; D. J. Harrison; P. Thibault, Application of microfluidic devices to proteomics research, *Mol. Cell. Proteomics* 2002, 1, 157-168.
28. H. Liu; C. Felten; Q. Xue; B. Zhang; P. Jedrzejewski; B. L. Karger; F. Foret, Development of multichannel devices with an array of electrospray tips for high-throughput mass spectrometry, *Anal. Chem.* 2000, 72, 3303-3310.
29. I. M. Lazar, R. S. Ramsey; J. M. Ramsey On-chip proteolytic digestion & analysis using "wrong-way-round" electrospray time-of-flight mass spectrometry, *Anal. Chem.* 2001, 73, 1733-1739.
30. D. Figeys, Adapting arrays and lab-on-a-chip technology for proteomics, *Proteomics* 2002, 2, 373-382.
31. M. Gustafsson, E. Togan-Tekin, R. Kånge, G. Ekstrand, P. Andersson, and S. Wallenborg, 50th Conference on Mass Spectrometry and Allied Topics, Orlando, Fla., USA, Jun. 2-6, 2002, ThPA004.
32. M. Holmquist, A. Palm, J. Engstrm, U. Selditz, and P. Anderson, 50th Conference on Mass Spectrometry and Allied Topics, Orlando, Fla., USA, Jun. 2-6, 2002, WPP238.
33. E. F. Petricoin III; A. M. Ardekani; B. A. Hitt; P. J. Levine; V. A. Fusaro; S. M. Steinberg; G. B. Mills; C. Simone; D.

A. Fishman; E. C. Kohn; L. A. Liotta, Use of proteomic patterns in serum to identify ovarian cancer, Lancet 2002, 359, 572-577.
34. E. P. Diamandis, Mass Spectrometry as a diagnostic and cancer biomarker discovery tool, Mol. Cell. Proteomics, 2004, 3(4), 367-378.
35. I. M. Lazar; B. L. Karger, Multiple open-channel electroosmotic pumping system for microfluidic sample handling," *Anal. Chem.*, 2002, 74(24), 6259-6268.
36. Microchip Integrated Multichannel Electroosmotic Pumping System, I. M. Lazar and B. L. Karger; patent application (priority date May 22, 2001, U.S. application 60/292,780).
37. I. M. Lazar; P. Trisiripisal; H. Sarvaiya, "Microfluidic Liquid Chromatography System for Proteomic Applications and Biomarker Screening," in press, Anal. Chem. 2006.
38. H. Sarvaiya; J. H. Yoon; I. M. Lazar, "Proteome Profile of the MCF7 Cancer Cell Line: A Mass Spectrometric Evaluation," accepted for publication, RCM 2006.

The invention claimed is:

1. A microfluidic device for on-chip complex sample processing, comprising:
a separation system including at least one pump and a separation channel for separating a complex liquid sample, wherein the separation channel includes a liquid chromatography medium;
an interface fluidly coupled to the separation channel and configured to transfer separated sample components from the separation channel into an array of microreservoirs;
wherein the interface comprises multiple microchannels having cross-sectional diameters or depths small enough to act as valves by way of hydraulic resistance, which substantially precludes leakage of the sample out of the separation channel and into the microchannels,
wherein different microreservoirs in said array of microreservoirs are connected by different microchannels positioned at different points along a length of said separation channel,
wherein the microchannels in the interface are adapted to translate separated components by an electroosmotic mechanism, such that when separation in the separation channel is completed, and the pump is turned off, a potential differential applied across the separation channel via the interface transfers the contents of the separation channel to the microreservoirs by said electroosmotic mechanism; and
wherein at least the separation channel, interface, and microreservoirs are disposed within the same chip, facilitating analyte detection directly on the chip.

2. The microfluidic device of claim 1, wherein the separation system comprises a high performance liquid chromatography (HPLC) system.

3. The microfluidic device of claim 1, wherein the interface comprises a pumping and/or valving interface.

4. The microfluidic device of claim 1, wherein the depth of the interface microchannels is less than 5 micrometers.

5. The microfluidic device of claim 1, wherein the length of the interface microchannels is less than 20 millimeters.

6. The microfluidic device of claim 1, wherein the lengths of the microchannels vary along the separation channel.

7. The microfluidic device of claim 1, wherein the interface includes a plurality of eluting microchannels coupled to the microreservoirs on one side of the separation channel and a plurality of rinsing microchannels coupled to a rinse channel on an opposite side of the separation channel.

8. The microfluidic device of claim 1, interfaced with a matrix assisted laser desorption ionization (MALDI), an atmospheric pressure (AP)-MALDI, subatmospheric MALDI, surface enhanced laser desorption ionization (SELDI), desorption/ionization on silicon (DIOS), laser desorption, or other mass spectrometry (MS) source.

9. The microfluidic device of claim 1, further comprising a means to interface with a sample component detection system for detection of analytes directly from the microreservoirs.

10. The microfluidic device of claim 1, wherein the microreservoirs are at least partially exposed to air.

11. The microfluidic device of claim 1, interfaced with a removal device operable to remove samples from the microreservoirs.

12. The microfluidic device of claim 1, comprising a multiplexed configuration of at least two or more separation channels and interfaces on the same chip, facilitating high-throughput analysis.

13. A method for microfluidic on-chip complex sample processing, said method comprising:
providing a microchip including:
a pump and a separation channel of a complex sample separation system, and
an array of microreservoirs, and an interface fluidly coupling the separation channel and array of microreservoirs;
wherein the interface comprises a plurality of microchannels having cross-sectional diameters or depths small enough to act as valves by way of hydraulic resistance, which substantially precludes leakage of the sample and/or sample components out of the separation channel and into the microchannels;
turning on the pump;
separating the sample components in the separation channel;
when the sample components are separated in the separation channel, turning off the pump; and
applying a potential differential across the separation channel and the interface to orthogonally transfer the separated sample components from the separation channel into the array of microreservoirs through an electroosmotic mechanism, facilitating analyte detection directly from the chip and further comprising performing HPLC in the separation channel.

14. The method of claim 13, further comprising using the interface as a pump or a valve to controllably translate the separated components.

15. The method of claim 13, wherein the step of using the interface includes transferring the separated sample components from the separation channel into the microreservoirs via the plurality of microchannels exhibiting hydraulic resistance.

16. The method of claim 13, further comprising evaporating eluent from the microreservoirs such that the sample components are deposited in the reservoirs and correspond to a plurality of spots.

17. The method of claim 13, further comprising performing matrix assisted laser desorption ionization (MALDI) mass spectrometry (MS) of the separated sample components directly from the microreservoirs.

18. The method of claim 13, further comprising interfacing the chip with an atmospheric pressure (AP)-MALDI, subatmospheric MALDI, surface enhanced laser desorption ionization (SELDI), desorption/ionization on silicon (DIOS), laser desorption, or other mass spectrometry (MS) source.

19. The method of claim 13, further comprising removing sample components from the chip for electrospraying, deposition onto another chip, or into another detection device.

20. A device for on-chip complex sample processing, said device comprising:
a separation means including a pump and a separation channel for receiving a complex sample and separating it into components wherein the separation channel includes a liquid chromatography medium;
an interface means coupled to the separation channel for transferring the separated sample components into a plurality of microreservoirs;
wherein the interface means comprises multiple microchannels having cross-sectional diameters or depths small enough to act as valves by way of hydraulic resistance, which substantially precludes leakage of the sample and/or separated components out of the separation channel and into the microchannels,
wherein different microreservoirs in said plurality of microreservoirs are connected by different microchannels in said interface means that are positioned at different points along a length of said separation channel,
wherein the microchannels in the interface means are adapted to translate separated components by an electroosmotic mechanism, such that when separation in the separation channel is completed, and the pump is turned off, a potential differential applied across the separation channel via the interface means transfers the contents of the separation channel to the microreservoirs by said electroosmotic mechanism, and
wherein at least the separation channel, interface means, and the plurality of microreservoirs are fabricated within a single chip, facilitating analyte detection on the chip.

21. An apparatus comprising the device of claim 20 interfaced with a removal means for removing separated components from the chip.

22. The device of claim 20, further comprising a multiplexed configuration of at least two or more separation channels and interface means on the same chip, facilitating high-throughput analysis.

23. A mass spectrometry (MS) interface disposed within a microfluidic device enabling high-throughput, on-chip complex sample processing, said interface in fluid connection with a separation channel of separation means which includes a pump communicating a sample to the sample channel, the interface and comprising a plurality of microchannels, the microchannels having cross-sectional diameters or depths small enough to act as valves by way of hydraulic resistance, which substantially precludes leakage of the sample and/or sample component out of the separation channel and into the microchannels, the interface, separation means, microchannels and microreservoirs all being fabricated on a single chip; and the microchannels configured to orthogonally transfer separated components from a complex sample separation channel to an array of microreservoirs using Electroosmotic Flow (EOF) after separation of sample components in the separation channel is complete, facilitating analyte detection directly on the chip wherein the separation channel includes a liquid chromatography medium; and wherein the different microreservoirs in said array of microreservoirs are connected by different microchannels positioned at different points along a length of said separation channel.

24. The interface of claim 23, wherein the interface is a pumping/valving interface.

25. The microfluidic device of claim 1, wherein the separation channel is 2-4 centimeters in length and 50 micrometers in depth, and the microchannels are 5-20 millimeters in length and 0.1-2 micrometers in depth.

26. A microchip integrated complex sample processing system comprising:
a separation system comprising:
one or more pumps, including an eluent inlet reservoir, an eluent outlet reservoir, the eluent inlet and outlet reservoirs being fluidly connected by hundreds/thousands of micro/nanochannels,
a mixer receiving outputs for said one or more pumps,
a separation channel,
a sample inlet reservoir,
a sample outlet reservoir, and
injector means for coupling the output of the mixer and a sample in the sample reservoir to the separation channel;
a waste reservoir and side packing channel located at a far end of the separation channel,
wherein the separation channel is a Liquid Chromatography (LC) separation system;
an interface, and
an array of microreservoirs, wherein the array of microreservoirs flanks the separation channel to one side, and the interface fluidly couples sections of the separation channel to the microreservoirs, the interface including a plurality of eluting microchannels between the separation channel and the microreservoirs, wherein different microreservoirs in said array of microreservoirs are connected by different microchannels positioned at different points along a length of said separation channel, wherein when separation in the main channel is completed, the pumps are turned off, and a potential differential is applied across the separation channel via the interface, transferring the contents of channel to reservoirs through an electroosmotic mechanism, facilitating analyte detection directly on the chip.

27. The microchip integrated complex sample processing system according to claim 26, wherein the interface is a Matrix Assisted Laser Desorption Ionization (MALDI) interface.

28. The microchip integrated complex sample processing system according to claim 26, wherein the injector means for coupling the output of the mixer and a sample in the sample reservoir to the separation channel is a double-T injector receiving the output of the mixer, one side of the double-T injector being coupled to the sample reservoir and the opposite side of the double-T injector being coupled to the sample waste reservoir via sample inlet and outlet channels, respectively, wherein the double-T injector outputs to the separation channel for separating the sample components.

29. The microchip integrated complex sample processing system according to claim 26, further comprising a rinsing channel longitudinally disposed along the opposite side of the separation channel and is fluidly coupled to the separation channel via a plurality of rinsing microchannels which help to flush the separation channel contents out of the separation channel, wherein the potential differential is applied between rinsing channel and each microreservoir and transfer of the contents of channel is further promoted with the aid of eluent coining from the rinsing channel.

30. The microchip integrated complex sample processing system according to claim 26, wherein the pumps are Electroosmotic Flow (EOF) pumps.

31. A method for microfluidic on-chip complex sample processing, comprising the steps of:
providing a separation system comprising:

one or more pumps, including an eluent inlet reservoir, and an eluent outlet reservoir, the eluent inlet and outlet reservoirs being fluidly connected by hundreds/thousands of micro/nanochannels a mixer receiving outputs from said one or more pumps, a separation channel, a sample inlet reservoir, a sample outlet reservoir, and injector means for coupling the output of the mixer and a sample in the sample reservoir to the separation channel;

a waste reservoir and side packing channel located at a far end of the separation channel;

wherein the separation channel is a Liquid Chromatography (LC) separation system, providing an interface, and providing an array of microreservoirs, wherein the array of microreservoirs flanks the separation channel to one side, and the interface fluidly couples sections of the separation channel to the microreservoirs, the interface including a plurality of eluting microchannels between the separation channel and the microreservoirs;

turning on said one or more pumps;

separating the sample components in the separation channel; and when separation in the separation channel is completed, turning pumps off;

applying a potential differential across the separation channel via the interface; orthogonally transferring separated sample components from the separation channel to reservoirs through an electroosmotic mechanism, facilitating analyte detection directly on the chip.

32. The method for microfluidic on-chip sample processing according to claim 31, wherein the step of providing an interface comprises the step of providing a Matrix Assisted Laser Desorption Ionization (MALDI) interface.

33. The method for microfluidic on-chip processing according to claim 31, wherein the step of providing a separation system provides a double-T injector for said injector means, said double-T injector receiving the output of the mixer, one side of the double-T injector being coupled to the sample reservoir and the opposite side of the double-T injector being coupled to the sample waste reservoir via sample inlet and outlet channels, respectively, wherein the double-T injector outputs to the separation channel for separating the sample components.

34. The method for microfluidic on-chip complex sample processing according to claim 31, wherein the separation system further comprises a rinsing channel longitudinally disposed along the opposite side of the separation channel and is fluidly coupled to the separation channel via a plurality of rinsing microchannels, and wherein the potential differential is applied between rinsing channel and each microreservoir, further comprising the steps of:

promoting transfer of the contents of channel with the aid of eluent coming from the rinsing channel; and flushing the separation channel contents out of the separation channel with eluent from the rinsing channel.

* * * * *